(12) United States Patent
Purvis et al.

(10) Patent No.: US 8,389,224 B2
(45) Date of Patent: *Mar. 5, 2013

(54) ASSAY FOR ANALYSIS OF FREE DRUG IN SAMPLES

(75) Inventors: Norman B. Purvis, Brentwood, TN (US); Gregory T. Stelzer, Brentwood, TN (US)

(73) Assignee: Laboratory Corporation of America Holdings, Burlington, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/088,841

(22) Filed: Apr. 18, 2011

(65) Prior Publication Data
US 2011/0212469 A1 Sep. 1, 2011

Related U.S. Application Data

(60) Continuation of application No. 11/927,223, filed on Oct. 29, 2007, now Pat. No. 7,943,327, which is a division of application No. 11/136,168, filed on May 24, 2005, now abandoned.

(60) Provisional application No. 60/573,783, filed on May 24, 2004.

(51) Int. Cl.
G01N 33/567 (2006.01)
G01N 21/76 (2006.01)
G01N 31/00 (2006.01)

(52) U.S. Cl. .... 435/7.2; 435/7.1; 435/40.51; 435/287.2; 436/501; 436/517; 436/538; 436/10; 436/164; 436/172; 424/9.2; 530/388.2

(58) Field of Classification Search ............... 435/6, 7.1, 435/7.2, 7.24, 40.51, 287.2; 436/501, 517, 436/522, 537, 538, 10, 17, 18, 63, 164, 172, 436/175–177; 422/73, 82.08; 530/388.2; 424/9.2

See application file for complete search history.

(56) References Cited

U.S. PATENT DOCUMENTS

| 5,597,688 | A | 1/1997 | Connelly et al. |
| 5,599,677 | A * | 2/1997 | Dowell et al. ................. 435/7.4 |
| 6,579,687 | B1 * | 6/2003 | Buechler et al. ............ 435/7.92 |
| 7,326,577 | B2 | 2/2008 | Shults et al. |
| 7,943,327 | B2 * | 5/2011 | Purvis et al. .................. 435/7.2 |
| 2001/0047441 | A1 | 11/2001 | Robertson |
| 2003/0103075 | A1 | 6/2003 | Rosselot |
| 2003/0133936 | A1 * | 7/2003 | Byrne et al. ............... 424/146.1 |
| 2005/0028221 | A1 | 2/2005 | Liu et al. |

FOREIGN PATENT DOCUMENTS

WO WO 96/41476 12/1996
WO WO 03/049438 6/2003

OTHER PUBLICATIONS

Francis et al. Rapid Singe-Step Method for Flow Cytometric Detection of Surface and Intracellular Antigens using Whole Blood, Cytometry, 25: 58-70 (1996).*
U.S. Appl. No. 60/512,834, filed Oct. 20, 2003, Shults et al.
Francis et al., "Rapid Singe-Step Method for Flow Cytometric Detection of Surface and Intercellular Antigens using Whole Blood," Cytometry, 1996, 25:58-70.

* cited by examiner

Primary Examiner — Gail R Gabel
(74) Attorney, Agent, or Firm — Kilpatrick Townsend & Stockton LLP

(57) ABSTRACT

Whole cell, simultaneous target and drug-target assay using differentially labeled antibodies and flow cytometry. First antibody binds to total target and second antibody binds to the drug binding site of the target, thus drug binding will competitively inhibit the second antibody allowing for a competitive inhibition assay of drug-target binding. The assay allows for whole cell analysis and even analysis of mixed populations of cells, yet provides detailed kinetic assessment of drug activity.

14 Claims, 6 Drawing Sheets

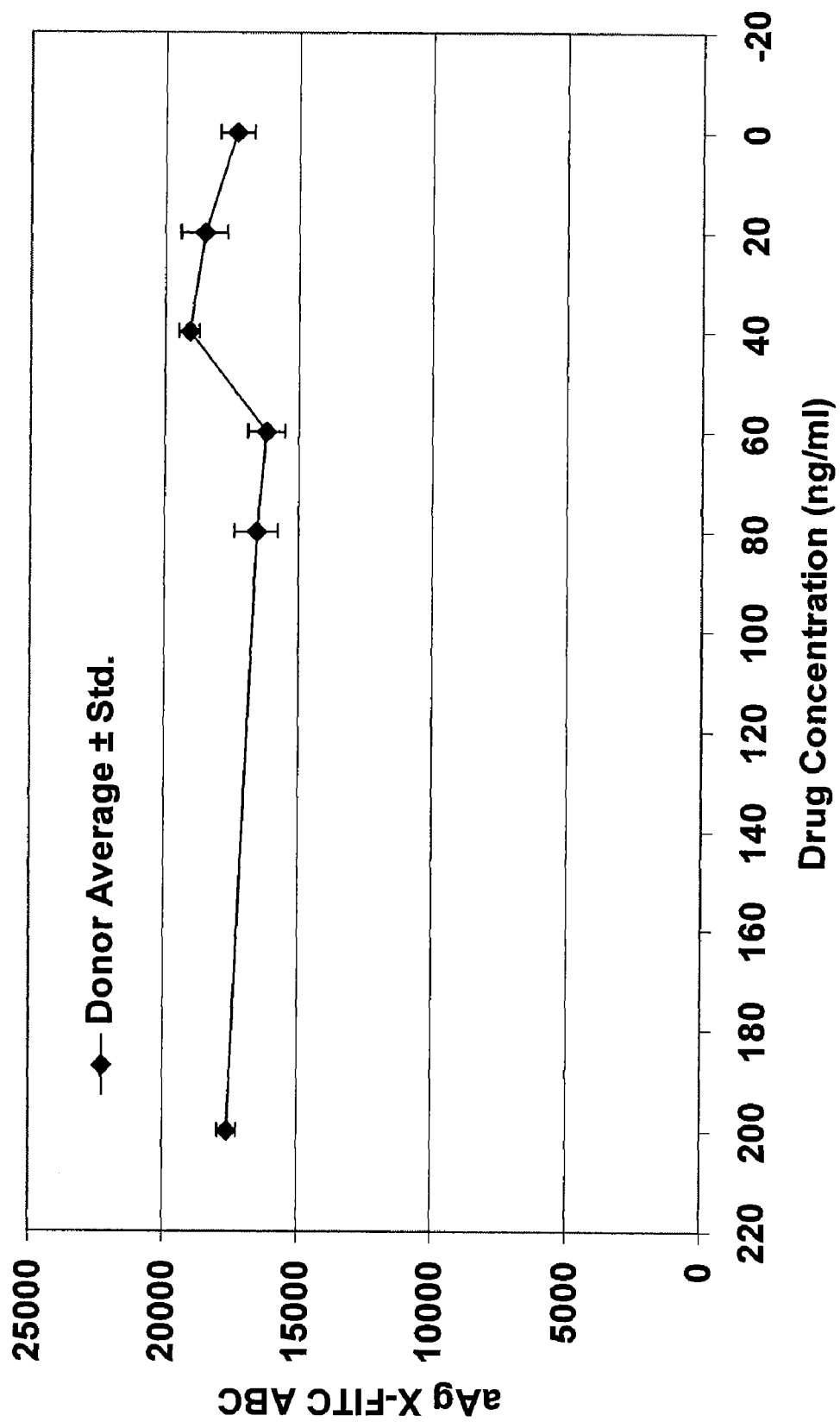
FIG. 3 Total Antibody Binding to Neutrophils

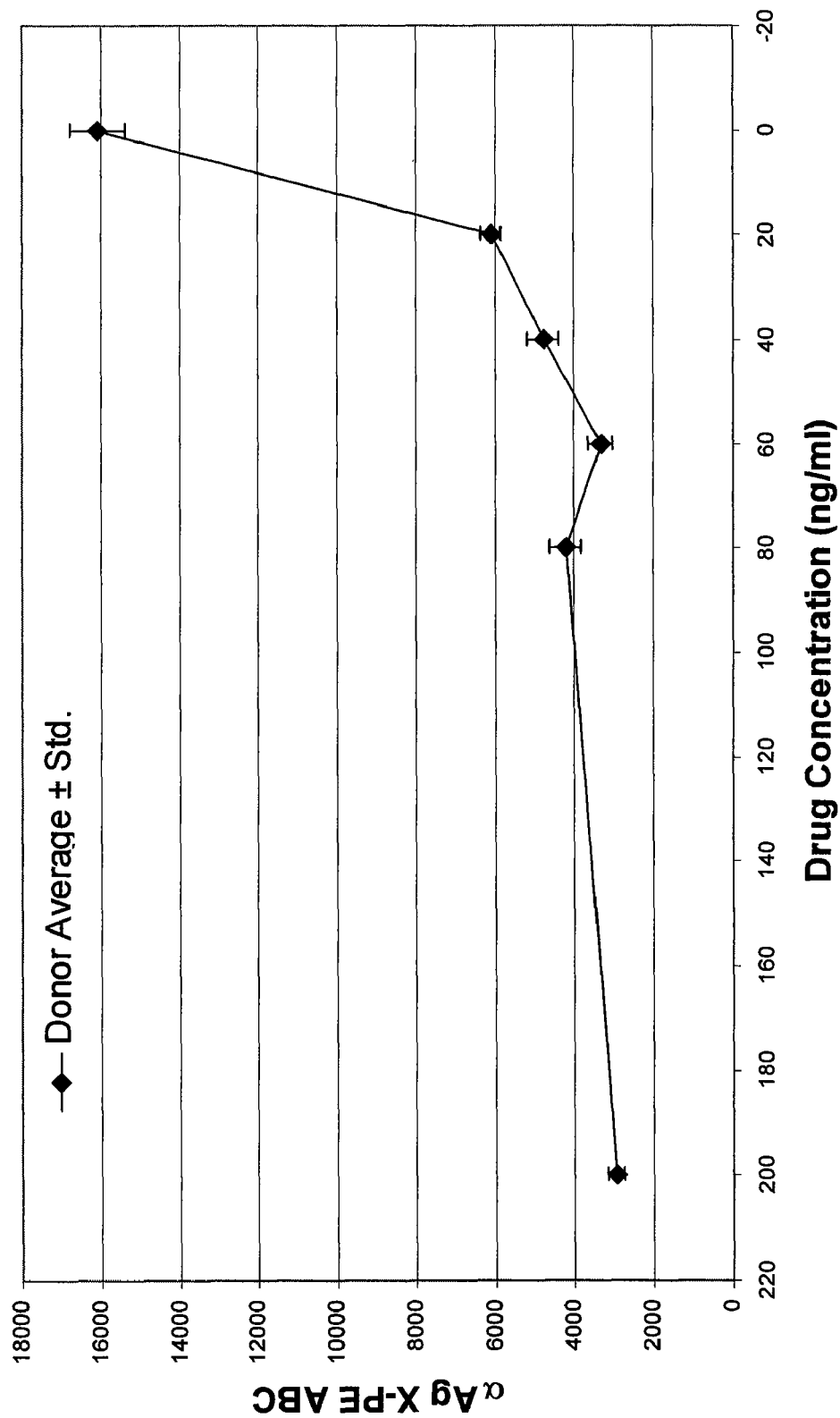
FIG. 4 Drug Sensitive Antibody Binding to Neutrophils

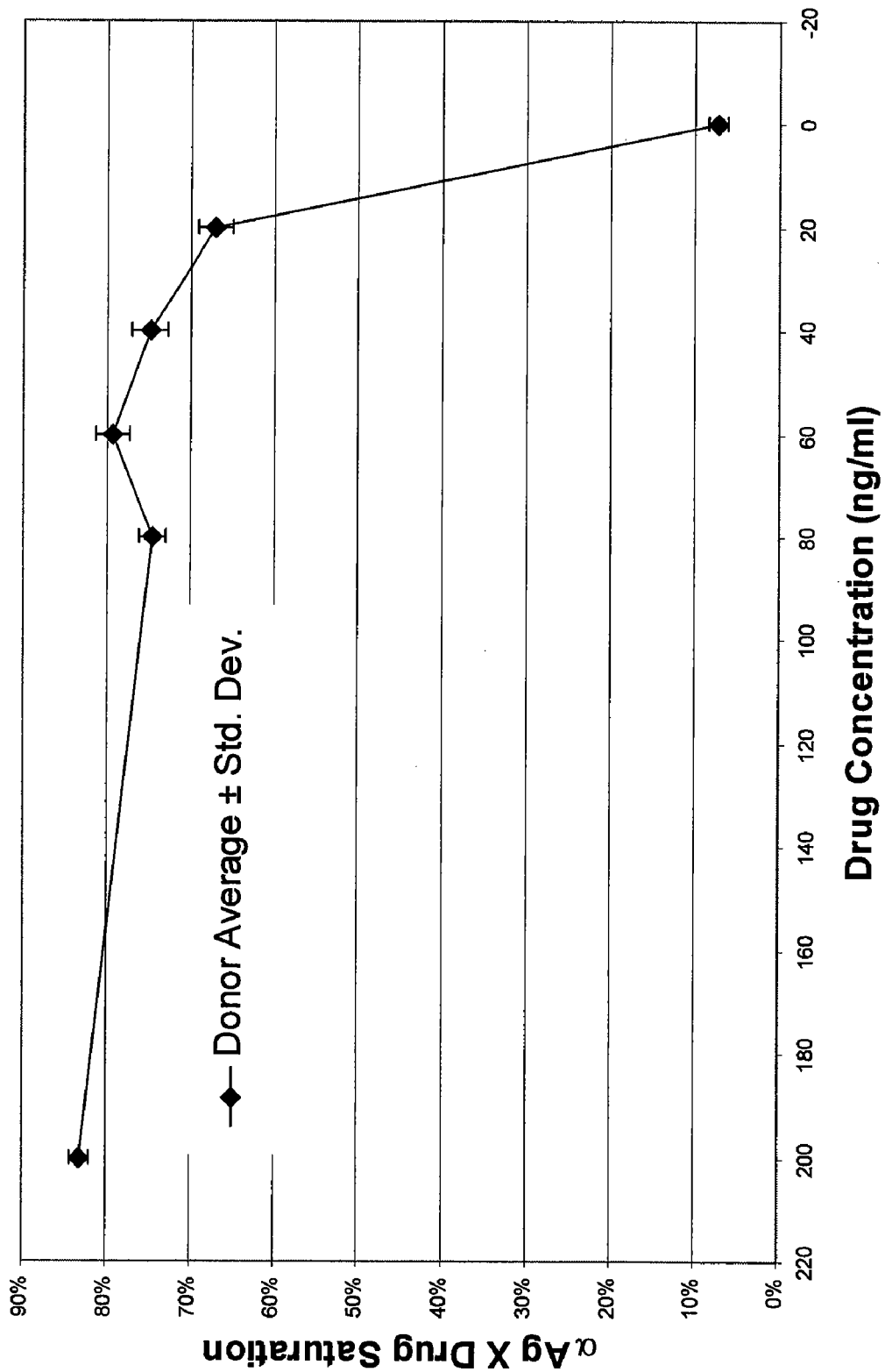
FIG. 5 % Saturation on Neutrophils

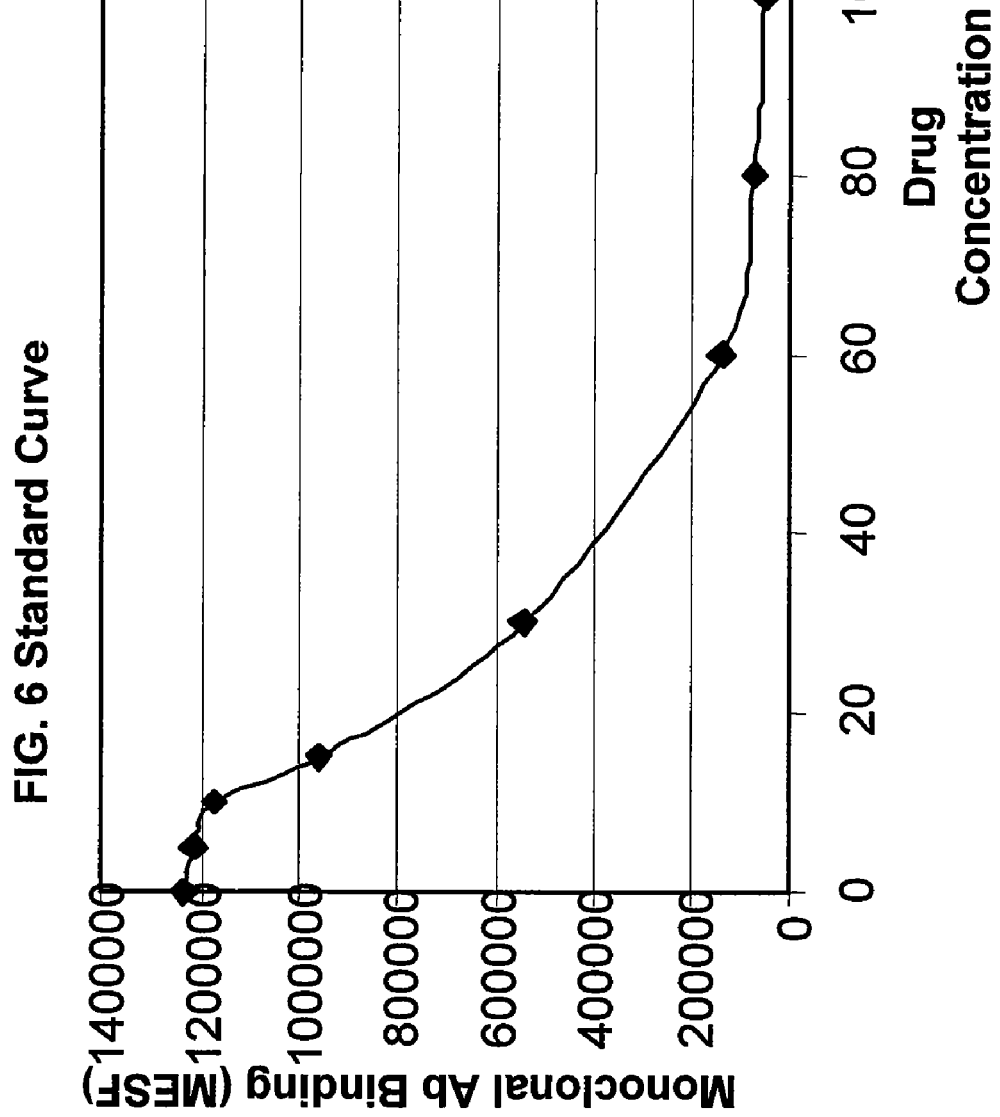

ASSAY FOR ANALYSIS OF FREE DRUG IN SAMPLES

This application is a continuation of U.S. patent application Ser. No. 11/927,223, filed Oct. 29, 2007, issued as U.S. Pat. No. 7,943,327 on May 17, 2011, which is a divisional of U.S. patent application Ser. No. 11/136,168, filed May 24, 2005, now abandoned, which claims the benefit of U.S. Provisional Application No. 60/573,783, filed May 24, 2004, each of which are incorporated by reference herein in their entireties.

FIELD OF THE INVENTION

The invention relates to a new cell based method of detecting or measuring drug activity, by simultaneously measuring target and target-drug combinations by flow cytometry. The method uses a pair of antibodies, one that is drug insensitive and will indicate total target level regardless of whether drug is present or not. The second is drug sensitive and will not bind to target at the same time that drug is bound to target. The drug and second antibody thus compete for the same or overlapping binding sites. Both antibodies can be simultaneously quantified when differentially labeled.

BACKGROUND

Previous methods of measuring drug activity have been laborious and complex. Typically, a drug target (the protein to which a drug binds in order to achieve its intended effect) is purified and the drug's effect on target activity over time is measured using increasing concentrations of the drug. Drug kinetics are then determined using standard data manipulations, such as the Scatchard or Lineweaver Burke plots.

However, protein purification and multiple assays make such methods laborious and not conducive to the high throughput generation of data. Further, purified proteins by definition are outside their normal body environment, and the changes in environment can complicate or change the way a protein behaves. This can result in misleading or incomplete information about a drug's activity and kinetics.

What is needed in the art is a method that allows the simultaneous detection of both total target and target-drug binding that would simplify and improve the accuracy of the determination of drug kinetics. It would be preferred if the method allowed such measurements without the prior purification of targets, for example in whole cells. It would be especially preferred if mixed populations of cells, such as are found in whole blood, could be studied without the need for prior separation of cell populations.

SUMMARY OF INVENTION

The following definitions are used herein:

"Anti-Total" antibody is an antibody that binds to the target at an epitope that is separate or independent from the drug binding site. Thus, such an antibody will detect "total" target level in a given sample.

"Anti-Free-Site" antibody is an antibody that binds to the drug binding or interaction site on the target, such that binding of the drug to the target and binding of the anti-free site antibody to the target are exclusive. Thus, such an antibody will detect drug-free target and be inhibited by drug binding. Bound target-drug concentration can thus be determined, as follows:

[Total target]=[Free-Site]+[Target-drug]

[Target-drug]=[Total target]−[Free-Site]

"Drug" is any pharmaceutical agent. Drugs as used herein also include the use of antibodies and their derivatives as therapeutic agents.

By "simultaneous" what is meant is that the measurements are taken at the same time from the same sample, whether or not the cytometer performs the measurements at the same actual instant or performs the measurements sequentially.

"Target" is defined as the protein that a given drug interacts with.

"Target-drug" is the target as it binds to or otherwise interacts with the drug of interest.

The following abbreviations are used in herein:

TABLE 1

Abbreviations

| Abbreviation | Expansion |
|---|---|
| ABC | Antibody Binding Capacity - The ABC is the number of monoclonal antibodies a sample will bind, and correlates to the number of antigens expressed on the cell surface. |
| Eff. F/P | The effective number of fluorochrome molecules conjugated per each antibody molecule determined by measured fluorescence intensity of antibody capture microspheres measured on a flow cytometer calibrated in units of fluorochrome specific MESF |
| F/P | Number of fluorochrome molecules conjugated per each antibody molecule determined by absorbance on a spectrophotometer. |
| FCS | Fetal Calf Serum |
| FSC-H | Forward angle light scatter |
| MESF | Molecules of Equivalent Soluble Fluorochrome. Corrects for changes in extinction coefficient, quenching, and small spectra shifts. Using the appropriate calibration controls, MESF and ABC can be calculated directly by the software that controls the cytometer. |
| MFI | Mean Fluorescence Intensity |
| PBS | phosphate buffered saline (200 mg/l KCl; 200 mg/l $KH_2PO_4$; 8 g/l NaCl; 2.16 g/l $Na_2HPO_4$ $7H_2O$, pH 7.4) |
| PD | Pharmacodynamics |
| PK | Pharmacokinetics |
| SSC-H | Right angle light scatter |
| αAgX | anti-antigen X - an antibody directed against a generic antigen called X |

The invention provides quantitative cell-based measurements of experimental drugs designed to bind to very specific protein "targets." It allows real time detection of target level and drug-bound target level, thus simplifying and improving on the prior art methods of studying drug kinetics.

The method generally is a cell based, two antibody assay that allows detection of total target in the sample and the simultaneous detection of that percentage of targets that are drug-bound and/or drug-free. Simultaneous detection is achieved by using different labels that can each be detected at the same time. In a preferred embodiment, the method uses flow cytometry to detect the different labels simultaneously.

The method generally involves the detection of total target using a labeled antibody that binds to the target. At the same time, target-drug binding pairs are detected with a second labeled antibody that binds to the drug binding site on the target. The principle assumption in the method is that binding of the drug to the target will result in the subsequent inhibition of an antibody directed at drug binding site of the target. Should this assumption hold true, the relationship between the drug blockade of antibody binding and the concentration of drug would form the basis of a very sensitive and specific "inhibition" immunoassay for bound drug.

Validation of the assay requires evaluation of several monoclonal antibodies in order to identify suitable antibody pairs, as follows: 1) a first antibody that is not inhibited by drug binding, thus providing measurement of total target level, and 2) a second antibody that is effectively inhibited by drug binding, thus proving the central assumption of competition between antibody and drug binding. If demonstrable antibody inhibition by drug binding is observed, then the assay can be calibrated by performing a drug inhibition standard curve. In this manner, the level of drug binding to target can be calculated based upon the level of antibody staining.

After antibody staining, the cells are fixed to allow for cytometric analysis. Both cell surface and internal targets can be studied, provided the fixation method is sufficiently gentle to retain cell morphology together with a good level of staining. The two antibodies are then simultaneously detected using flow cytometry, wherein the cytometer is appropriately gated to allow detection of the two labels at the same time. In a preferred embodiment, additional labels can be used to type the cells according to surface antigens. Thus, the cells need not be separated prior to study and complex samples, such as whole blood, can be studied.

The labels should be chosen with the operating characteristics of the cytometer in mind such that there is sufficient separation of signal so as to allow the cytometer to distinguish between the two or more signals. Many such labels are known in the art, including fluorescent isothiocyanate (FITC, aka fluorescein), Phycoerythrin (PE); CY5™ PE; CY7™ PE; TEXAS RED™ (TR); Allophycocyanin (APC); CY5™; CY7™ APC; CASCADE BLUE™; and the like.

A great many conjugated antibodies are commercially available and these can easily be screened to identify antibody pairs with the requisite binding characteristics (Total and Free-Site binding). Those antibodies that are not conjugated can easily be conjugated with an appropriate dye using one of the many available conjugation kits. Commercial suppliers will also provide custom antibodies on demand.

We have exemplified the method with whole blood by first lysing the RBCs in isotonic solution, and then by separating the cells of interest based on gating according to surface antigen staining. For example, using CD14 as a surface antigen, it was possible to separately analyze both monocytes and neutrophils in the same blood sample. The method can be generally applied and other cell populations, such as bone marrow, can also be studied.

In this novel approach to cell-based analysis of drug pharmacodynamics (PD), cells taken from subjects exposed to various drug concentrations can be assayed to determine the proportion of total available drug targets per cell that are occupied by drug (% saturation). In addition, should the target be expressed at various levels in different populations of cells within the sample (or a different levels between patients), the method allows for simultaneous and independent quantification of target saturation on each different cell population.

An alternative application of this method is for the analysis of free drug in plasma or serum of subjects exposed to various drug dosage regimens. Data from this assay is useful in pharmacokinetic (PK) modeling of functional drug activity. The PK application utilizes a cell line that constitutively expresses the receptor protein target to which the drug binds. Incubation of the cell line with a standard range of drug concentrations followed by staining of the cells with fluorochrome-conjugated drug sensitive monoclonal antibodies allows for the construction of a very specific standard curve of antibody fluorescence as it inversely relates to drug concentration. Subsequent to the construction of the standard curve, it is possible to derive the amount of drug in specimens of unknown concentration by extrapolation of the degree of drug-induced inhibition of antibody fluorescence to drug concentration as defined by the standard curve.

In one embodiment, the invention is a method of measuring drug activity in whole cells by reacting cells with labeled anti-Total antibody (detects total target in the sample) and with a labeled anti-Free-Site antibody (detects only drug free target). The cells are fixed and both antibodies are quantified by flow cytometry. The level of drug bound target is proportional to the level of anti-total antibody staining minus the anti-Free-Site antibody staining. The method can also be applied to mixed populations of cells if the cells are pre-typed by staining with a third antibody. The method is also applicable to both cell surface and internal targets.

The method can be used to determine a variety of drug kinetic parameters, including pharmacokinetics and pharmacodynamics. It can also be used to determine circulating free drug levels in serum or plasma if used with a standard curve of anti-Free-Site antibody binding versus drug concentration.

BRIEF DESCRIPTION OF THE DRAWINGS

FIG. 1A shows side-scatter (SSC-H) on the x-axis plotted against forward-scatter (FSC-H) on the y-axis. All nucleated cells remaining in the lysed blood sample are indicated. The cytometer is then gated to separate the APC-labeled and non-labeled cells in FIG. 1B, which shows side-scatter (SSC-H) on the x-axis plotted against the APC labeled anti-CD14 antibody scatter ("CD14-APC") on the y-axis. The separated monocytes (moderate side-scatter, CD14+) and neutrophils (high side-scatter, CD14−) are indicated.

FIG. 3. Total Antibody Binding to Neutrophils: Drug concentration in ng/ml on the x-axis is plotted against αAgX-FITC ABC. The antibody staining is constant, thus this antibody detects total AgX levels and is not drug sensitive.

FIG. 4. Drug Sensitive Antibody Binding to Neutrophils: Drug concentration in ng/ml on the x-axis is plotted against αAgX-PE ABC. The antibody staining decreases with increasing drug concentration, thus this antibody binds to the drug binding site and the drug competes with antibody binding.

FIG. 5. Percent Saturation on Neutrophils: Drug concentration in ng/ml on the x-axis is plotted against percent saturation (αAg Drug saturation) on the y-axis. Percent saturation is calculated by: % Saturation=[(αAgX-FITC ABC−αAg X-PE ABC)/(αAg X-FITC ABC)]×100.

FIG. 6. Standard Curve: Standard curve of free drug concentration verses fluorescence (MESF) of the drug sensitive anti-AgX antibody on a target cell line.

DETAILED DESCRIPTION

Figure 1:
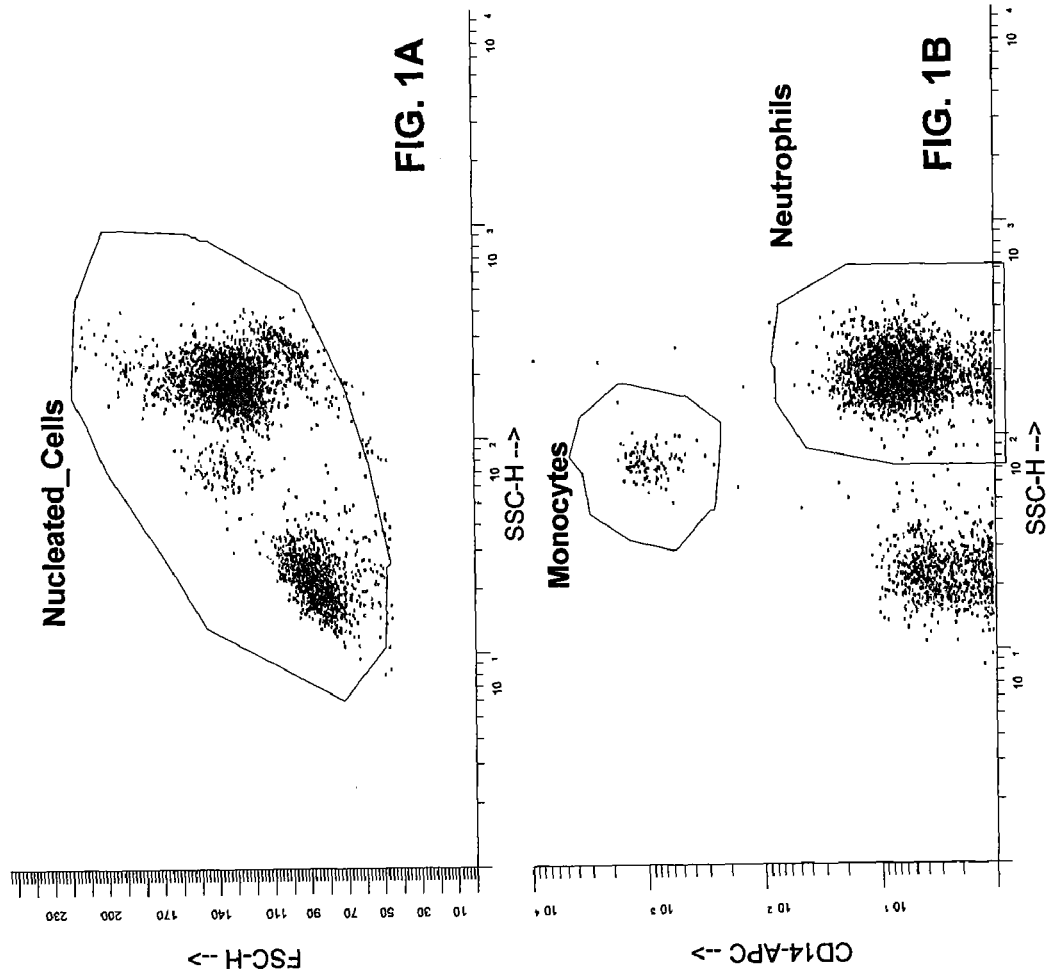
FIG. 1. Flow Cytometry.

The present invention is exemplified with respect to CD11b and a proprietary drug known by the code name Neutrophil Inhibitory Factor. However, the invention has general applicability to the study of any drug-target combinations for which suitable antibody pairs can be identified. The following examples describe the invention as practiced in additional detail, but should not be construed as limiting.

Example 1

Antibody Optimization

The following method was employed to validate the method of the invention using the targets and antibodies described in Table 2, below. However, it can be applied to any novel combinations of antibodies to find suitable antibody pairs useful for any target-drug combinations of interest.

Commercially available conjugated antibodies against various antigens (generically called AgX) were identified and ordered for evaluation in the method of the invention. Non-conjugated, purified antibodies as well as proprietary pharmaceutical grade antibodies can also be obtained for evaluation and potential custom conjugation.

All anti-AgX antibodies against were evaluated in triplicate in the presence and absence of saturating concentrations of the appropriate drug (in each instance, the drug is specific for a single epitope on the protein AgX) by performing individual multi-point two-fold serial dilutions of each antibody. Additional cell subtype specific antibodies labeled with different fluorochromes may be added to each tube to allow the study of specific populations of cells as necessary.

Antibody titration data was plotted to show 1) staining intensity versus antibody staining concentration, 2) percent positive staining versus concentration and 3) the signal to noise ratio versus concentration. These plots aided in the identification of the optimal staining concentration of each antibody, indicated whether saturation staining was possible for each antibody and indicated whether the particular antibody measured total AgX expression or was inhibited by the presence of drug.

If multiple anti-Total AgX antibodies and anti-Free-Site AgX antibodies were identified, the antibodies that provided the best signal to noise ratio were chosen. In cases were the commercially available antibodies are sub-saturating or not available in the ideal fluorochrome conjugate, custom conjugates can be ordered or prepared in-house. The effective F/P (effective fluorescence to probe ratio) was determined for each of the anti-Total and anti-Free-Site antibodies identified for use in the drug saturation assay.

Drug specific antibody panels were and will continue to be developed. Anti-Total and anti-Free-Site antibodies were used to allow monitoring of drug occupancy on the cells of interest during PK and PD experiments. Ex-vivo spiking experiments using appropriate biological samples spiked at varied concentrations of the drug were used to verify operational characteristics of the antibody cocktails and proper drug saturation calculations based on anti-Total and anti-Free-Site antibody measurements.

The antibodies, target and drugs validated to date for use in the methods of the inventions include:

TABLE 2

Exemplary Target-Drug Combinations and Antibody Pairs

| Target | Drug | Anti-Total Antibody | Vendor (Cat. #) | Anti-Free Site Antibody | Vendor (Cat. #) |
|---|---|---|---|---|---|
| CD11b | Neutrophil inhibitory factor | anti-human CD11b-FITC | Beckman Coulter (IM0530) | anti-human CD11b-PE | BD Biosciences (30455S) |
| CD11a | chimeric humanized anti-CD11a | anti-human CD11a-PE | BD Biosciences (555384) | anti-human CD11a-FITC | Dako-Cytomation (F0712) |
| CD18 | Proprietary | anti-human CD18-PE | BD Biosciences (555924) | anti-human CD18-FITC | Dako-Cytomation (F0839) |
| CD22 | Proprietary | anti-human CD22-FITC | Serotec (MCA553F) | anti-human CD22-PE | Immunotech (IM1835) |
| CD25 | Proprietary | anti-human CD25-PE | BD Biosciences (555432) | anti-human CD25-PE | BD Biosciences (341009) |

Example 2

Additional Antibody Pairs

Additional antibody pairs that can be used in the general method of the invention for particular target and drug combinations can be identified using the method described generally in Example 1. Some possible combinations are listed in Table 3. However, the combinations are unlimited and additional combinations can identified by searching MEDLINE, ATCC or the web.

TABLE 3

Additional Target-Drug Combinations and Antibody Pairs

| Target | Drug | Antibodies |
|---|---|---|
| CD20 | Rituximab, Bexxar | PRO70769, Rituximab, Bexxar (Tositumomab), B1, Immu-106, Ibritumomab, H147, L27 |
| CD52 | Campath-1H (Alemtuzumab) | Campath-1H |
| CD33 | In Development | HB-10306, Mab 251, M195, huM195, PC251, L4F3 |
| CD4 | In Development | OKT4, TNX-355, HuMax-CD4, GK1.5, W3/25, YTS177.9, ORTHOCLONE OKTcdr4a |
| CD3 | In Development | HB231, HB10166, UCHT1, PS1, OKT3 |
| CD14 | In Development | HB-247, HB-246, UCHM-1, IC14, M5E2, MΦP9 |
| CD30 | In Development | cAC10-vcMMAE, SGN-30, Ki-1, K0145-3, HSR-4, BER-H2 |
| HLA-Dr | Hu1D10 | Hu1D10, L243, BRA30, 1D09C3, TNB-211, 1D10, LN3 |
| MAP Kinase (e.g., MAPK1-18) | In Development | SC-154 |
| RAF-1 | In Development | Ab-2 |
| AKT | In Development | SKB-1 |
| BCL-2 | In Development | YTH-10C4, 124, 10C4 |
| Chemokine Receptors (e.g. CCR1 to CCR7) | Sch-417690/Sch-D, GSK-873, 140 UK-427, 857 (CCR5) | S3504 (CCR1), 48607 (CCR2), 83103 (CCR3), Ig1 (CCR4), 140706 (CCR6), 11A9 (CCR6), 3D12 (CCR7), 112509 (CCR9) |
| ESRA | fulvestrant | 6F11, ER1D5, AER311, ER88 |

Example 3

Flow Cytometry

Although the invention has been exemplified with respect to several antibody pair-drug combinations, as indicated in Table 2, only the data from a single study (CD11b) are presented herein for simplicity. These results are representative, although the details for each study will vary. The protocols described are also exemplary, but cell harvesting, antibody staining, fixation, and gating parameters should be (and were) optimized for each experiment.

General Protocol: For analysis of whole blood by flow cytometry, the following protocol was employed: 100 μl of whole blood was sterilely collected for each data point. For each sample, 2 ml of standard culture media plus or minus drug was added to the blood and the tubes vortexed briefly to mix. The samples were then incubated to allow drug binding for 1 hr at 37° C.

Next the cells were stained with the appropriate antibody or antibodies. A saturating amount (as determined in the titration evaluation of each antibody against the target) of desired antibody was added to each tube, and the tubes were incubated at 37° C. for 1 hr. Immediately after incubation, the cells were collected by centrifugation, and erythrocytes were lysed using a standard ammonium chloride lysing procedure.

The cells were collected by centrifugation, and 2 ml of cold PBS+2% FCS was added to each tube. The tubes were placed in the dark at room temperature for at least 10 minutes and up to 1 hour to allow RBC lysis upon resuspension of the fixed whole blood samples in this isotonic solution. The cells were collected again and washed once or twice with PBS+2% FCS with a final resuspension in 1% paraformaldehyde in PBS. The samples were thus ready for data collection.

We have used the BECKMAN COULTER™ Epics XL or BECTON DICKINSON™ FACS Calibur Flow cytometer herein, but any properly quality controlled flow cytometer that satisfies established windows of analysis can be used, provided the laser excitation lines and filter configurations are correct for the excitation and detection of all fluorescence labels used in the assay. The analysis that is actually performed will vary depending on the experiment being performed, which of the cellular parameters are of interest, and the actual labels employed. In general, we collect 30,000 ungated events. Data was analyzed in WinList (VERITY SOFTWARE™) and Excel (MICROSOFT™) or equivalent. Exemplary results for the CD11b/Neutrophil Inhibitory Factor experiments are shown in FIGS. 1 through 6.

Separation of Monocytes and Neutrophils: In the first experiment, whole blood was stained with anti-CD14-APC, the cells were fixed, the RBCs lysed, and the remaining nucleated cells analyzed by cytometer. FIG. 1A shows light scatter patterns of the nucleated cells (leukocytes) stained with anti-CD14-APC. In FIG. 1B, an electronic gating window was constructed around the nucleated cells to separate the cells based on the expression of the CD14 marker. The APC signal was used to separate the leukocytes into CD14 positive cells (monocytes) and CD14 negative (neutrophils).

Additional electronic gating windows can be applied to these two cell populations for simultaneous and independent analysis of the binding of the drug sensitive antibody (anti-Free-Site antibody) and the drug insensitive antibody (anti-Total) on each cell type respectively. This type of analysis is shown in FIG. 2.

Antibody Pair Binding: As above, whole blood was incubated with or without drug, stained with the appropriate antibodies, fixed, lysed and analyzed. This particular experiment was designed so that drug insensitive antibody (anti-Total) was labeled with FITC ($\alpha$AgX-FITC) and drug sensitive antibody (anti-Free-Site) was labeled with PE ($\alpha$AgX-PE). However, other labels could be used. Blood was treated with three different concentrations of drug and only the neutrophil results are shown in FIG. 2.

Figure 2:
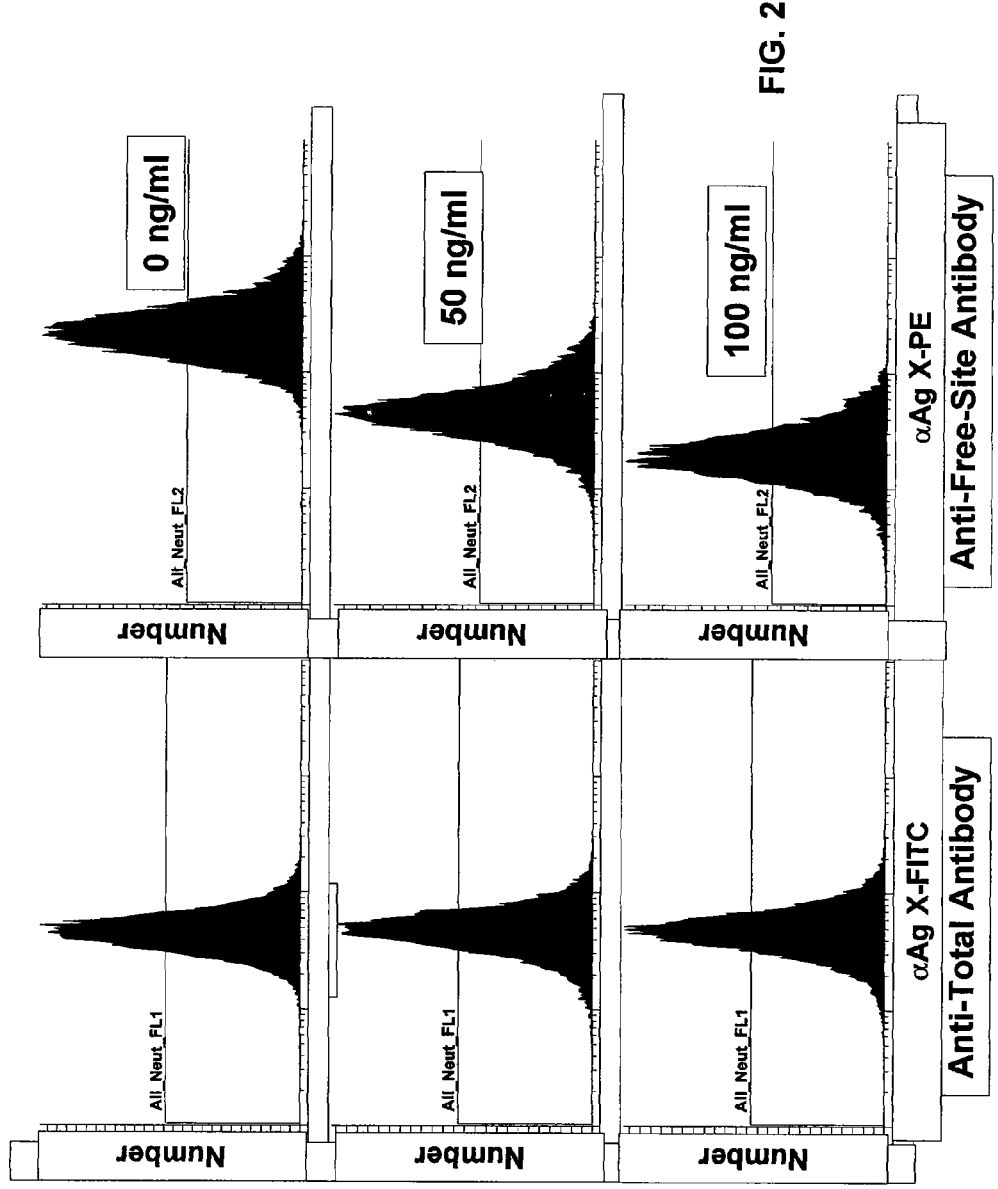
FIG. 2. Antibody Binding Characteristics: Fluorescence intensity (MESF) on the x-axis is plotted against the total number of cells (Number) on the y-axis. The left panel indicates αAgX-FITC, which is the drug insensitive antibody (anti-Total). The right panel is αAgX-PE, which is the drug sensitive antibody (anti-Free-Site). Varying amounts of drug were added to each sample (0-Top, 50 ng/ml-middle, 100 ng/ml-bottom). Inhibition of the drug sensitive antibody by drug is indicated by a loss of fluorescence intensity in the staining by the anti-Free-Site antibody, shown by the peak shifting to the left (right panel).

The histograms in FIG. 2 show fluorescence intensity at ~525 nm (left panel, FITC signal) and ~575 nm (right panel, PE signal) on the x-axis plotted against the number of cells counted (Number) on the y-axis. As the drug level increases, the $\alpha$AgX-PE peak shifts to the left indicating a decrease in fluorescence intensity. Thus, anti-Free-Site antibody binding decreases due to the competition by the drug for the drug sensitive epitope. In contrast, the fluorescence intensity of the anti-AgX-FITC stain was invariant at all drug concentrations, indicating constant binding of this antibody to the drug insensitive epitope.

Target-Drug Binding: In the next two experiments, broader ranges of drug concentrations were investigated. Whole blood was incubated with various concentrations of drug ranging from 0-200 ng/ml, followed by antibody staining, fixing, lysis and analysis as described above. The data in FIG. 3 demonstrates constant binding of drug insensitive (anti-Total) antibody over a broad range of drug concentration. In contrast, the data in FIG. 4 demonstrates a dose dependent inhibition of the binding of the drug sensitive anti-AgX-PE (anti-Free-Site) to neutrophils.

The data from FIGS. 3 and 4 were used to calculate percent saturation as shown in FIG. 5. Percent Saturation was calculated as the anti-AgX-FITC signal minus the anti-Ag X-PE signal divided by the anti-AgX-FITC signal times 100. The data demonstrates that the drug causes a dose dependent inhibition of drug sensitive antibody binding to neutrophils.

Standard Curve: A target cell line (HL-60) was exposed to different drug concentrations ranging from 0 to 150 ng/ml. Subsequent to drug incubation, the cells were stained with drug sensitive anti-AgX and binding of the fluorescent antibody was quantified on the cytometer as described above and used to prepare this standard curve. Note: This curve was performed using monoclonal antibody binding intensity (MESF). However, the same curve may be constructed using monoclonal ABC.

Unknown concentrations of drug in patient specimens can be derived by extrapolation of quantitative fluorescence of the anti-AgX antibody to the respective drug concentration on this standard curve.

Example 4

Intracellular Targets

Although the invention has been thus far exemplified with surface targets, such as CD11b, it is also possible to study internal targets using the methods of the invention because fixatives are now available that allow the detection of internal epitopes. Cells are permeabilized with agents such as 0.05% TRITON X-100™ in PBS, stained with antibody and then fixed. For example, PERMEAFIX™ or PERMIFLOW™ at mild denaturation temperatures preserves cell morphology and thus allows subsequent analysis by flow cytometry. Such methods are described in more detail in co-pending application 60/512,834 filed Oct. 20, 2003.

Acceptable fixatives are defined herein as fixatives that allow both cell fixation and permeation, while retaining cell surface morphology and DNA and RNA content, sufficient to allow separation of cells based on light scatter, surface epitopes and/or nucleic acid content. An acceptable fixative contains 0.75-0.85% formaldehyde, 25-30 mM DNBS, 6.8-7% DMSO and 0.08-0.1% TWEEN 20™ detergent. A preferred fixative is PERMIFLOW™. Mild denaturing temperatures are those temperature that improve access to internal antigens, without compromising cell morphology, surface antigens or nucleic acid content. Preferred temperatures range from 39 to 43° C., and most preferred 43° C.

What is claimed is:

1. A method of measuring free drug present in a biological sample from a subject, comprising:
   (a) combining a biological sample from a subject who is taking the drug with a target cell, wherein the biological sample comprises a biological fluid sample, and wherein the target cell expresses a target that interacts with the drug to bind to at least a portion of the drug present in the biological fluid sample,
   (b) mixing the target cell of step (a) that has been combined with the free drug present in the biological sample with a labeled anti-Free-Site antibody, wherein the anti-Free Site antibody is a monoclonal antibody that recognizes and binds to an epitope on the target when the drug is not bound to the target but is competitively inhibited by binding of the drug to the target;
   (c) washing away unbound anti-Free-Site antibody from the target cell of step (b);
   (d) fixing the target cell of step (c);
   (e) quantifying the amount of anti-Free-Site antibody binding to the target cell of step (d) by flow cytometry; and
   (f) determining the amount of free drug present in the biological sample by comparing the amount of anti-Free-Site antibody bound to the target cell as quantified in step (e) to a standard curve of pre-determined amounts of Anti-Free-Site antibody bound to target cells previously exposed to known amounts of the drug, wherein the standard curve illustrates a correlation between the amount of Anti-Free Site antibody bound to target cells and the amount of drug reacted with the target cells, and correlating the amount of anti-Free-Site antibody bound to the target cell to the amount of free drug present in the biological sample based on the standard curve.

2. The method of claim 1, further comprising reacting the target cell of step (a) with a labeled anti-Total antibody and quantifying the amount of anti-Total antibody bound to the target cell to determine the total amount of target expressed by the target cell wherein the anti-Total antibody comprises a monoclonal antibody that binds to an epitope on the target that is different from both the epitope bound by the anti-Free-Site antibody and the epitope bound by the drug.

3. The method of claim 2, wherein the anti-Total antibody is conjugated to a dye or fluorescent label that is different than the dye or fluorescent label conjugated to the anti-Free Site antibody.

4. The method of claim 3, wherein the anti-Free-Site antibody and the anti-Total antibody are each conjugated to a different dye or fluorescent label.

5. The method of claim 2, wherein the anti-Total Antibody comprises an anti-human CD11 a antibody, an anti-human CD11b antibody, an anti-human CD18 antibody, an anti-human CD22 antibody, an anti-human CD25 antibody, an anti-human CD20 antibody, an anti-human CD52 antibody, an anti-human CD33 antibody, an anti-human CD4 antibody, an anti-human CD3 antibody, an anti-human CD14 antibody, an anti-human CD30 antibody, an anti-human HLA antibody, an anti-human MAP kinase antibody, an anti-human RAF-1 antibody, an anti-human AKT antibody, an anti-human BCL-2 antibody, an anti-human chemokine receptor antibody, or an anti-human ESRA antibody.

6. The method of claim 1, wherein the target cell of step (a) and the target cells of step (f) are permeabilized target cells.

7. The method of claim 6, wherein the target cell of step (a) is permeabilized prior to step (b).

8. The method claim 1, wherein the anti-Free Site antibody is conjugated to a dye or fluorescent label.

9. The method of claim 1, wherein the anti-Free-Site Antibody comprises an anti-human CD11a antibody, an anti-human CD11b antibody, an anti-human CD18 antibody, an anti-human CD22 antibody, an anti-human CD25 antibody, an anti-human CD20 antibody, an anti-human CD52 antibody, an anti-human CD33 antibody, an anti-human CD4 antibody, an anti-human CD3 antibody, an anti-human CD14 antibody, an anti-human CD30 antibody, an anti-human HLA antibody, an anti-human MAP kinase antibody, an anti-human RAF-1 antibody, an anti-human AKT antibody, an anti-human BCL-2 antibody, an anti-human chemokine receptor antibody, or an anti-human ESRA antibody.

10. The method of claim 1, wherein the standard curve of step (f) is generated by the method comprising:
    (i) exposing separate aliquots of target cells to known amounts of the drug, wherein the target cells are the same type of target cell combined with the biological sample from the subject;
    (ii) combining the aliquots of the target cells of (i) with the labeled Anti-Free-Site antibody;
    (iii) washing away the unbound anti-Free-Site antibody from the aliquots of the target cells of (ii);
    (iv) fixing the aliquots of the target cells of step (iii);
    (v) quantifying the amount of Anti-Free-Site antibody binding to the aliquots of the target cells of step (iv); and
    (vi) preparing the standard curve showing the relationship between the drug concentration and the quantified binding of the anti-Free-Site antibody to the aliquots of target cells of step (v).

11. The method of claim 10, wherein the aliquots of target cells of (i) are exposed to a permeabilization agent prior to step (ii).

12. The method of claim 1, wherein the biological sample comprises blood, plasma, serum, or bone marrow.

13. The method of claim 1, wherein step (e) is performed by flow cytometry.

14. The method of claim 1, wherein the target cell comprises a cell line that constitutively expresses the target to which the drug binds.

* * * * *

UNITED STATES PATENT AND TRADEMARK OFFICE
CERTIFICATE OF CORRECTION

PATENT NO. : 8,389,224 B2
APPLICATION NO. : 13/088841
DATED : March 5, 2013
INVENTOR(S) : Norman B. Purvis et al.

It is certified that error appears in the above-identified patent and that said Letters Patent is hereby corrected as shown below:

In the Specification

Column 3, Line 5, Please change "a" to "at."

In the Claims

Column 10, Line 47, Claim 11, Please add "step" before "(i)."

Signed and Sealed this
Seventeenth Day of September, 2013

Teresa Stanek Rea
*Deputy Director of the United States Patent and Trademark Office*